United States Patent
Hall et al.

(10) Patent No.: US 7,964,276 B2
(45) Date of Patent: Jun. 21, 2011

(54) FASTENING SYSTEM WITH AUTO-ADHESIVE LAYER EXPOSED THROUGH RUPTURABLE COVER LAYER

(75) Inventors: Gregory K. Hall, Menasha, WI (US); Michael J. Garvey, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1309 days.

(21) Appl. No.: 11/214,513

(22) Filed: Aug. 30, 2005

(65) Prior Publication Data
US 2007/0048479 A1 Mar. 1, 2007

(51) Int. Cl.
*B32B 7/12* (2006.01)
*B32B 15/04* (2006.01)

(52) U.S. Cl. ...... 428/354; 428/40.1; 428/41.7; 428/343; 428/355 R; 428/355 RA; 428/355 BL

(58) Field of Classification Search .......... 604/389, 604/390; 428/40.1, 41.7, 343, 354, 355 R, 428/355 RA, 355 BL; 524/504, 505
See application file for complete search history.

(56) References Cited

U.S. PATENT DOCUMENTS

| | | | | |
|---|---|---|---|---|
| 3,379,562 A | * | 4/1968 | Freeman | 428/41.3 |
| 3,441,638 A | * | 4/1969 | Patchell et al. | 264/154 |
| 3,616,154 A | * | 10/1971 | Dow et al. | 428/134 |
| 3,967,624 A | * | 7/1976 | Milnamow | 604/378 |
| 4,063,559 A | | 12/1977 | Tritsch | |
| 5,085,655 A | | 2/1992 | Mann et al. | |
| 5,372,865 A | * | 12/1994 | Arakawa et al. | 428/41.5 |
| 6,261,278 B1 | * | 7/2001 | Chen et al. | 604/389 |
| 6,419,667 B1 | | 7/2002 | Avalon et al. | |
| 6,461,715 B1 | * | 10/2002 | Guenther et al. | 428/131 |
| 2002/0095130 A1 | * | 7/2002 | Seitter et al. | 604/389 |
| 2005/0132543 A1 | | 6/2005 | Lindsay et al. | |
| 2005/0177127 A1 | | 8/2005 | Ashton et al. | |

FOREIGN PATENT DOCUMENTS
WO WO-0243638 A2 6/2002
WO WO-2007027235 A1 3/2007

OTHER PUBLICATIONS
A. Dahiya, M.G. Kamath, R.R. Hegde. "Melt Blown Technology." Apr. 2004. Accessed Jul. 30, 2009.*
International Search Report and Written Opinion mailed Oct. 18, 2006 in PCT/US2006/016909, 12 pages.

* cited by examiner

*Primary Examiner* — Callie E Shosho
*Assistant Examiner* — Nicholas Kokkinos
(74) *Attorney, Agent, or Firm* — Dority & Manning, P.A.

(57) ABSTRACT

A fastening system that includes an auto-adhesive layer and a cover layer. The cover layer engages the auto-adhesive layer such that the auto-adhesive layer is exposed as the cover layer is stretched. In some embodiments, stretching the cover layer causes the cover layer to rupture (i.e., tear) so that the auto-adhesive layer may be exposed for subsequent bonding. The term "auto-adhesive" refers to self-adhesive properties of a polymeric material where an auto-adhesive is substantially non-adhesive with respect to many other materials. Also disclosed is a method of joining a fastening system to an item. The method includes positioning the fastening system near the item. The method further includes exposing an auto-adhesive layer by stretching a cover layer that is engaged with the auto-adhesive layer and then engaging the auto-adhesive layer on the fastening system with an auto-adhesive layer on the item.

10 Claims, 5 Drawing Sheets

FASTENING SYSTEM WITH AUTO-ADHESIVE LAYER EXPOSED THROUGH RUPTURABLE COVER LAYER

FIELD OF THE INVENTION

This invention relates to a fastening system, and in particular to a fastening system that joins different items together, or different portions of the same item together.

BACKGROUND OF THE INVENTION

Many products include fastening systems that are used to join different items together, or different portions of the same item together. As an example, a fastening system is typically used to adhere different portions of a diaper together when a diaper is placed onto a child.

Some fastening systems are formed as an adhesive tape that includes a substrate which has a tacky material covering some (or all) of the substrate. The tacky material covers one or both sides of the substrate depending on the type of fastening system.

One drawback with using adhesive tapes to join items together is that the tapes readily stick to unwanted areas which make them cumbersome to handle. As an example, in some fastening systems that are used in diapers, the tacky material can undesirably stick to a child's tender skin.

Another drawback with using adhesive tapes is that the tacky material which is used in many adhesive tapes is easily contaminated (e.g., with dirt, baby powder, etc.). The ability of an adhesive tape to effectively secure items together is reduced as the tacky material becomes contaminated.

Some adhesive tapes try to minimize unwanted sticking and/or contamination of the tacky material by placing a temporary cover over the tacky material. One disadvantage of incorporating a cover for the tacky material is that the consumer needs to perform some labor in order to get the adhesive tape ready for fastening. In addition, the consumer needs to dispose of a cover once it is removed from the rest of the adhesive tape.

Another type of fastening system incorporates hook and loop type elements. These types of systems typically require the hook elements to be on one item (or section) so that they can be secured to the loop elements on another item (or section).

One drawback with using hook and loop type elements is that the hook and loop type elements can be abrasive if they engage items other than each other. As an example, when hook and loop type elements are used in diapers, the hook and loop type elements can undesirably abrade a child's tender skin. In addition, hook and loop type elements are often relatively stiff such that they are difficult to incorporate into many types of products.

One important consideration with many products is the aesthetic appeal of the product. It can be to difficult to integrate either adhesive tapes or hook and loop type elements into many products because the addition of these types of fastening systems often has a negative impact on the aesthetic appeal of the products.

SUMMARY OF THE INVENTION

The present invention provides a convenient and cost-effective fastening system. The fastening system may be used to join one item to another item, or to join one portion of an item to another portion of the same item. As an example, the fastening system may be used to secure one portion of a diaper to another portion of a diaper.

The fastening system includes an auto-adhesive layer and a cover layer. The cover layer engages the auto-adhesive layer such that the auto-adhesive layer is exposed as the cover layer is stretched. In some embodiments, stretching the cover layer causes the cover layer to rupture (i.e., tear) so that the auto-adhesive layer may be exposed for subsequent bonding to an item that includes a similar auto-adhesive material.

As used herein, the terms "auto-adhesive" and "auto-adhesion" refer to self-adhesive properties of a polymeric material. An auto-adhesive may be in the form of films, layers or coatings. An auto-adhesive is substantially non-adhesive with respect to many other materials. Some auto-adhesives may (or may not) be repeatedly adhered together and separated at service (e.g., room) temperature.

As used herein, the Peak Load of Auto-adhesive Strength represents a force that is required to separate a layer that is attached to itself. In some embodiments, the auto-adhesive layer may exhibit a Peak Load of Auto-adhesive Strength value that is greater than about 400 grams per inch width of the layer.

In some embodiments, the cover layer may be formed of a thermoplastic polymer that includes polymer chains which are oriented in a substantially uniform direction. The auto-adhesive layer may be exposed by stretching the cover layer in a direction that is perpendicular to the substantially uniform direction of the polymer chains in the cover layer. In other embodiments, the cover layer may be formed of a nonwoven material (e.g., a melt-blown fibrous material).

The fastening system may further include an elastic layer. The elastic layer may provide the fastening system with a degree of elasticity that would otherwise not be possible with the auto-adhesive and the cover layer alone. The elastic layer has a hysteresis of less than 50% and a set value of less than about 15%.

In another form, the present invention relates to a method of joining a fastening system to an item. The method includes positioning a fastening system near the item that is to be joined to the fastening system. The method further includes exposing an auto-adhesive layer by stretching a cover layer that is engaged with the auto-adhesive layer and then engaging an auto-adhesive layer on the fastening system with an auto-adhesive layer on the item. In some forms of the method, exposing the auto-adhesive layer by stretching the cover layer may include rupturing the cover layer.

In some embodiments of the method, the cover layer may include a thermoplastic polymer that has polymer chains which are oriented in a substantially uniform direction X. Therefore, exposing the auto-adhesive layer may include exposing the auto-adhesive layer by stretching the cover layer in a direction that is perpendicular to the substantially uniform direction of the polymer chains.

In another form, the present invention relates to a fastening method that includes positioning a first auto-adhesive layer near a second auto-adhesive layer and engaging the first auto-adhesive layer with the second auto-adhesive layer. The method further includes applying a force to the first and second auto-adhesive layers to stretch the first and second auto-adhesive layers and increase a bonding area between the first and second auto-adhesive layers. The method may further include removing the force F from the first and second adhesive layers.

Each of the auto-adhesive layers may include imperfections that negatively impact the degree of contact in the bonding area between the auto-adhesive layers. As the auto-adhesive layers are stretched, the bonding area between the auto-adhesive layers increases, and the imperfections on the auto-adhesive layers are somewhat smoothed out so that there is improved contact between the auto-adhesive layers in the enlarged bonding area. The improved contact in the bonding area results in improved joint strength between the auto-adhesive layers.

The first auto-adhesive layer may be attached to a first elastic layer, and the second auto-adhesive layer may be attached to a second elastic layer such that applying a force to the first and second auto-adhesive layers also includes applying a force to the first and second elastic layers. The first and second elastic layers may each have a hysteresis of less than 50% and a set value of less than 15%.

DEFINITIONS

The terms "elastic" and "elastomeric" when referring to a fiber, film or nonwoven fabric (or layer) means a material that upon application of a biasing force is stretched in at least one direction by at least 50% and which will recover at least 50 percent of its elongation upon release of the biasing force after about a minute (under ambient conditions).

"Elastic tension" refers to the amount of force per unit width required to stretch an elastic material (or a selected zone thereof) to a given percent elongation.

"Elongation" refers to the capability of an elastic material to be stretched a certain distance.

The terms "recover" or "retract" refer to relaxation of a stretched material upon removal of a biasing force. As an example, if a material has an unbiased length of one (1) inch and was elongated by 50 percent, the material would have a stretched length that is 50% greater than the relaxed length. If after releasing the biasing force the material recovers to a length of one and one tenth (1.1) inches, the material would have recovered 80 percent (0.4 inch) of its elongation.

As used herein, the term "set" refers to retained elongation in a material following an elongation and a recovery (i.e. after a material has been stretched and allowed to relax).

As used herein, the term "permanent set" refers to the retained set after a period of time following retraction (e.g., 1 minute).

As used herein, the terms "machine direction" or MD mean the direction along the length of a web, layer or film in the direction in which it is produced, and the terms "cross-machine direction," or CD mean the direction across the width of fabric (i.e. a direction generally perpendicular to the MD).

As used herein, the term "thermoplastic" refers to a material that softens when exposed to heat and which substantially returns to a non-softened condition when cooled.

DESCRIPTION OF THE INVENTION

Figure 1:
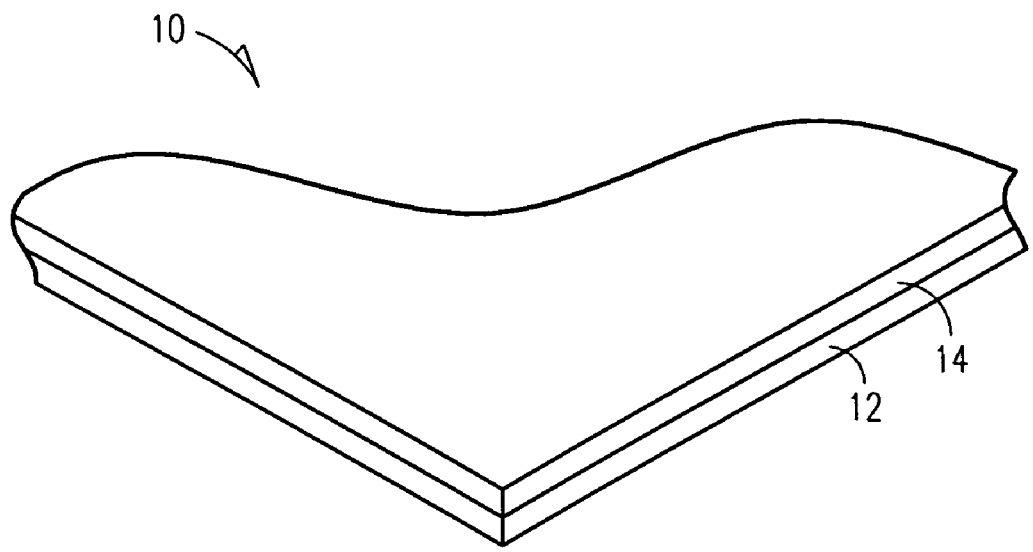
FIG. 1 is a perspective view illustrating an example fastening system.
Figure 2:
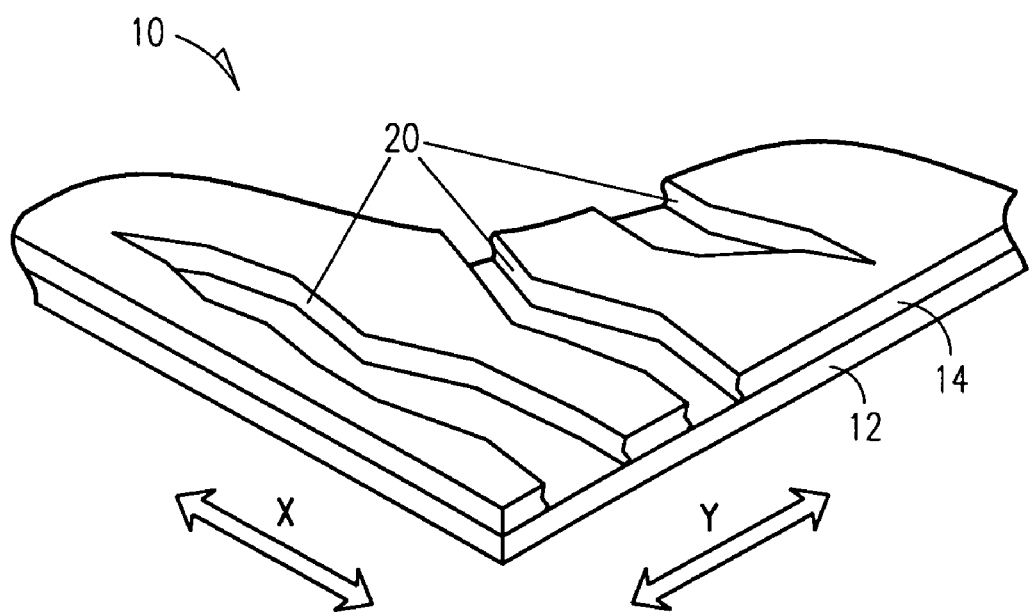
FIG. 2 is a perspective view of the fastening system shown in FIG. 1 with the cover layer of the fastening system ruptured to expose an auto-adhesive layer.

FIGS. 1 and 2 illustrate a fastening system 10 that includes an auto-adhesive layer 12 and a cover layer 14. The cover layer 14 engages the auto-adhesive layer 12 such that the auto-adhesive layer 12 is exposed as the cover layer 14 is stretched (see FIG. 2). In some embodiments, stretching the cover layer 14 may cause the cover layer 14 to rupture (i.e., tear) thereby forming ruptures 20 so that the auto-adhesive layer 12 is exposed for subsequent bonding to an item that includes a similar auto-adhesive material.

Although only a portion of the auto-adhesive layer 12 and the cover layer 14 are shown in FIGS. 1 and 2, it should be noted that the auto-adhesive layer 12 and the cover layer 14 may be any size or shape (e.g., square, rectangular, circular). In addition, the auto-adhesive layer 12 and the cover layer 14 may be a variety of different thickness depending on the application where the fastening system is used. The cover layer 14 may be attached to the auto-adhesive layer 12 through any method that is known now or discovered in the future. As used herein, "layer" refers to any type of substrate including laminates of one or more types of material.

As used herein, the terms "auto-adhesive" and "auto-adhesion" refer to self-adhesive properties of a polymeric material. An auto-adhesive may be in the form of films, layers or coatings. An auto-adhesive is substantially non-adhesive with respect to many other materials. Some auto-adhesives may (or may not) be repeatedly adhered together and separated at service (e.g., room) temperature. Service temperature indicates the intended temperature or temperature range of use for an auto-adhesive by an end user.

In some embodiments, the auto-adhesive layer 12 may be formed a polymeric material that includes thermoplastic elastomers. As an example, the thermoplastic elastomers may have molecules that include sequential arrangements of unique combinations of monomer units. The thermoplastic elastomers should have relatively stable auto-adhesive properties and be substantially non-adhesive with respect to other materials. It may also be desirable if the thermoplastic elastomers can be formed as laminates with other polymeric materials having pre-selected properties.

The auto-adhesive layer 12 may include a thermoplastic elastomer that has physical cross-links which restrict the elastomer mobility (i.e., flow). Restricting the elastomeric mobility may promote the auto-adhesive properties of a thermoplastic elastomer.

Some example thermoplastic elastomers that may be used in the auto-adhesive layer 12 include multiblock copolymers of radial, triblock and diblock structures including non-rubbery segments of mono- and polycyclic aromatic hydrocarbons, and more particularly, mono- and polycyclic arenes. As examples, mono- and polycyclic arenes may include substituted and unsubstituted poly(vinyl)arenes of monocyclic and bicyclic structure.

The thermoplastic elastomers may include non-rubbery segments of substituted or unsubstituted monocyclic arenes of sufficient segment molecular weight to assure phase separation at room temperature. As examples, monocyclic arenes may include polystyrene and substituted polystyrenes including monomer units such as styrene and alkyl substituted styrene (e.g., alpha methylstyrene and 4-methylstyrene). Other examples include substituted or unsubstituted polycyclic arenes that have monomer units (e.g., 2-vinyl naphthalene and 6-ethyl-2-vinyl naphthalene).

The thermoplastic elastomers may also include rubbery segments that are polymer blocks which may be composed of homopolymers of a monomer, or a copolymer that includes two or more monomers selected from aliphatic conjugated diene compounds (e.g., 1,3-butadiene and isoprene). Some example rubbery materials include polyisoprene, polybutadiene and styrene butadiene rubbers. Other example rubbery materials include saturated olefin rubber of either ethylene/butylene or ethylene/propylene copolymers, which may be derived from the corresponding unsaturated polyalkylene moieties (e.g., hydrogenated polybutadiene and polyisoprene).

In some embodiments, the thermoplastic elastomer may be part of a styrenic block copolymer system that includes rubbery segments which may be saturated by hydrogenating unsaturated precursors (e.g., a styrene-butadiene-styrene (SBS) block copolymer that has center or mid-segments which include a mixture of 1,4 and 1,2 isomers). A -butadiene-styrene (SBS) block copolymer that includes center or mid-segments which have a mixture of 1,4 and 1,2 isomers may be hydrogenated to obtain (i) a styrene-ethylene-butylene-styrene (SEBS) block copolymer; or (ii) a styrene-ethylene-propylene-styrene (SEPS) block copolymer.

In other embodiments, the auto-adhesive layer 12 may include a mixture of a polyethylene and a block copolymer. As an example, the auto-adhesive layer 12 may include a mixture of one or more block copolymers selected from the group consisting of poly(styrene)-co-poly (ethylene-butylene)-co-poly(styrene) copolymer, poly(styrene)-co-poly (ethylene-butylene) copolymer, and a polyethylene polymer. In some embodiments, the one or more block copolymers may be between about 30 weight percent to about 95 weight percent of the auto-adhesive layer 12, and the polyethylene polymer may be between about 5 weight percent to about 70 weight percent of the auto-adhesive layer 12 (wherein all weight percents are based on the total weight amount of the block copolymer and the polyethylene polymer that are present in the auto-adhesive layer).

As used herein, the Peak Load of Auto-adhesive Strength represents a force that is required to separate a layer that is attached to itself. When the layer is used as an auto-adhesive layer, the Peak load of Auto-adhesive Strength should meet the adhesive strength requirement for a particular application. If an auto-adhesive layer is used in a fastening system, the Peak Load of Auto-adhesive Strength for the auto-adhesive layer needs to be high enough to prevent the fastening system from opening during use. Auto-adhesive layers that exhibit too low of a Peak Load of Auto-adhesive Strength may not be suitable for some fastening system applications.

The auto-adhesive layer 12 readily bonds to other auto-adhesive layers (not shown in FIGS. 1 and 2) with a strength that is greater than the strength which is generated when the auto-adhesive layer is bonded to any other type of material (e.g., a bonding strength that is at least twice as great). As an example, the auto-adhesive layer 12 may exhibit a Peak Load of Auto-Adhesive Strength value that is greater than about 400 grams per inch width of the layer (about 157 grams per centimeter width of the layer), and up to about 2000 grams per inch width of the layer (about 787 grams per centimeter width of the layer). The method by which the Peak Load of Auto-Adhesive Strength value for a layer is determined is set forth in U.S. Pat. No. 6,261,278.

In some embodiments, the cover layer 14 includes a thermoplastic polymer that has polymer chains which are oriented in a substantially uniform direction (see, e.g., arrow X in FIG. 2). Depending on the application where the fastening system 10 is to be used, the auto-adhesive layer 12 may be exposed by stretching the cover layer 14 in a direction that is perpendicular (see arrow Y in FIG. 2) to the substantially uniform direction X of the polymer chains.

Some example materials that may be used for the cover layer 14 include high density polyethylene, polypropylene, polystyrene, metallocene polypropylene (singe site catalyzed), low density polyethylene, linear low polyethylene, ethylene butyl acrylate, ethylene vinyl acetate (EVA) and polylactic acid (and blends thereof). The type of material that is selected for the cover layer 14 will be selected based on processing parameters and the physical properties of the material (among other factors). In some embodiments, the cover layer 14 may have a density that is greater than 1.0 grams per cubic centimeter.

In still other embodiments, the cover layer 14 may include a non-woven material. Some example non-woven materials include polyester and metallocene polyethylene, polypropylene and other polyolefin blends.

Figure 3:
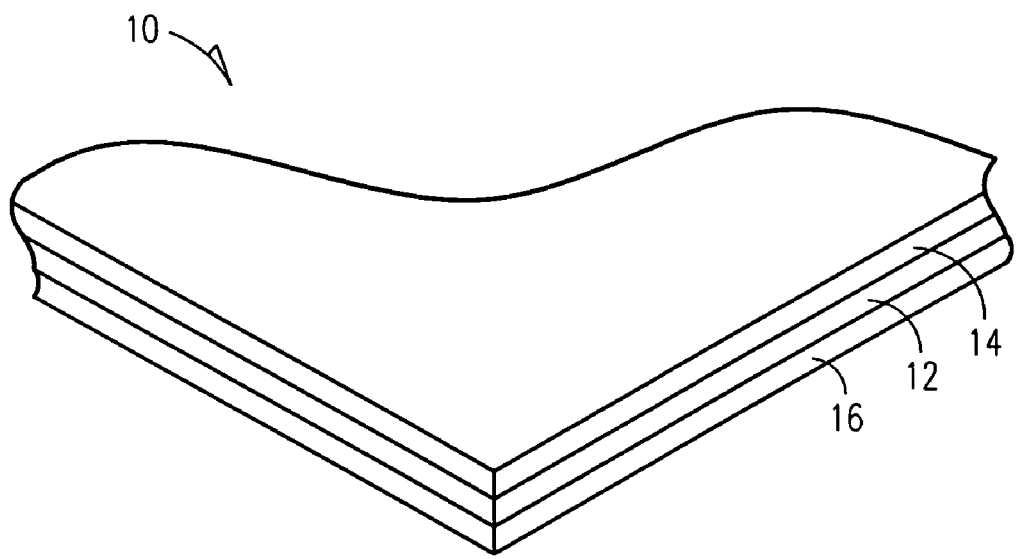
FIG. 3 is a perspective view illustrating another example fastening system.
Figure 4:
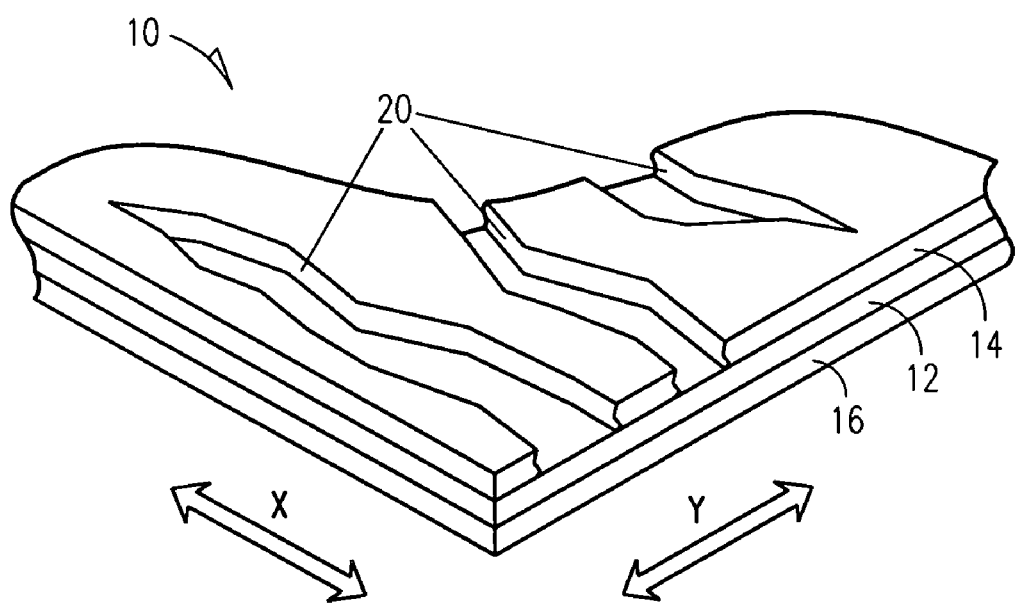
FIG. 4 is a perspective view of the fastening system shown in FIG. 3 with the cover layer of the fastening system ruptured to expose an auto-adhesive layer.
Figure 5:
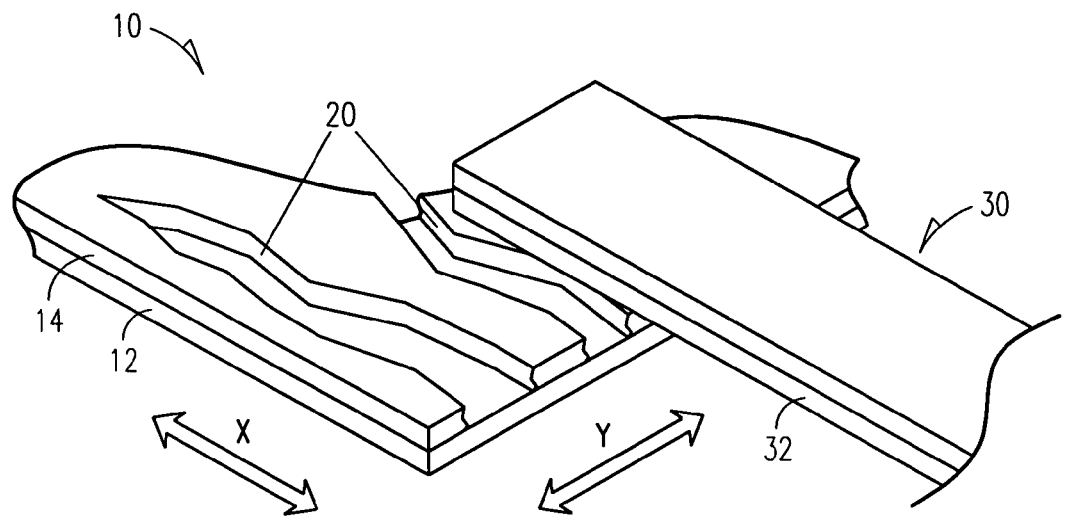
FIG. 5 is a perspective view of the fastening system shown in FIG. 2 with the fastening system secured to another item that includes an auto-adhesive layer.
Figure 6:
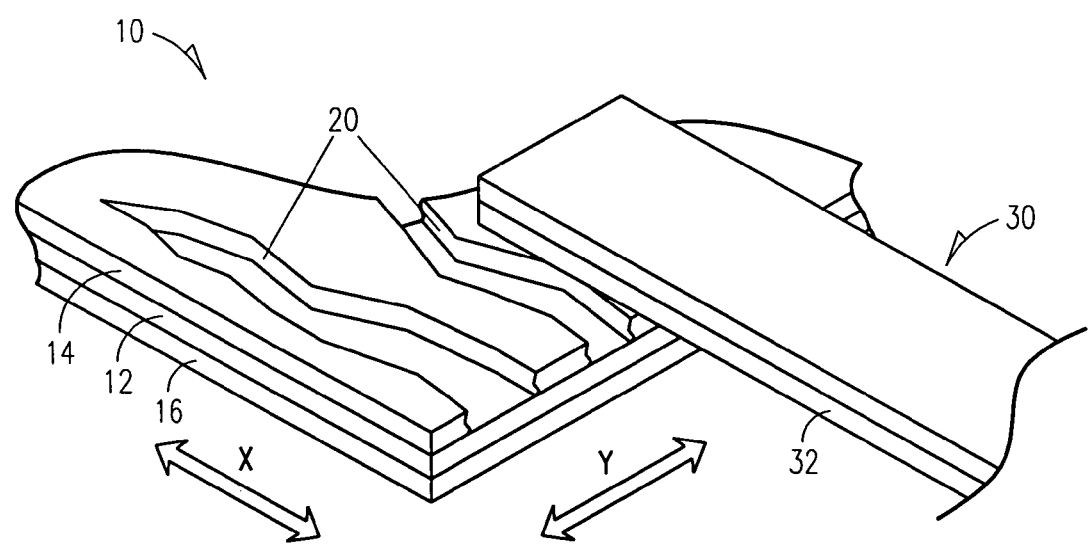
FIG. 6 is a perspective view of the fastening system shown in FIG. 4 with the fastening system secured to another item that includes an auto-adhesive layer.

As shown in FIGS. 3 and 4, the fastening system 10 may further include an elastic layer 16. The elastic layer 16 may provide the fastening system 10 with a degree of elasticity that would otherwise not be possible with the auto-adhesive layer 12 and the cover layer 14 alone. In the example embodiment that is illustrated in FIGS. 3 and 4, the elastic layer 16 is in contact with the auto-adhesive layer 12 such that the auto-adhesive layer 12 is between the cover layer 14 and the elastic layer 16.

In some embodiments, the elastic layer 16 has a hysteresis of less than 70%, and more preferably less than 50%; and a set value of less than 30%, and more preferably less than about 15%. Hysteresis may be determined according to one or more of the following test methods:

I. Stress-Strain Cycle Test Method (2 Cycles to 100% Elongation, 3rd Elongation to Break)

An elastic composite sample (3 inch wide·times·6 inch long) is placed in the clamps of a constant rate of extension (CRE) load frame. One example load frame is a SINTECH tensile tester which is available from the MTS Systems Corporation, Eden Prairie, Minn. (model SYNERGIE 200).

A four inch gauge length is situated between the sample grips and the sample is elongated at 500 mm/min. (i.e., approximately 20 inches/minute) to 100% elongation (i.e., 8 in. between the sample grips). The cross-head is returned to the original 4 inch gauge length position to complete the cycle. Another cycle to 100% elongation is performed. The sample is then elongated a third time until the sample breaks.

Data points are recorded and plotted in grams force on the Y axis and % elongation on the X axis (data acquired at a rate of 100 data points per cycle). The percent set is determined as the percent elongation at which the specimen reaches zero load on the return portion (i.e. retraction) of the cycle. Testing is conducted at approximately 73° F. and about 50 percent relative humidity.

Results

The loading and unloading energy are calculated using the test results by integrating the area under the respective curves. Percentage hysteresis is then calculated according to the following equation:

$$\% \text{ Hysteresis} = [(\text{Loading Energy} - \text{Unloading Energy})/\text{Loading Energy}] \times 100$$

II. Stress-Strain Elongation Test Method (to 2000 Grams or Break)

An elastic composite sample (3 inch wide·times·6 inch long) is placed in the clamps of a constant rate of extension (CRE) load frame. One example load frame is a SINTECH tensile tester which is available from the MTS Systems Corporation, Eden Prairie, Minn. (model Synergic SYNERGIE 200).

A four inch gauge length is situated between the sample grips and the sample is elongated at 500 mm/min. (i.e., approximately 20 inches/minute) to 100% elongation (i.e., 8 in. between the sample grips) until 2000 grams tension are reached (or until breakage occurs). The data points are recorded and plotted in grams force on the Y axis and % elongation on the X axis. Testing is conducted at approximately 73° F. and about 50 percent relative humidity.

Some example materials that may be used for the elastic layer 16 are styrenic block copolymers that include hydrogenated polyisoprene polymers such as styrene-ethylenepropylene-styrene (SEPS), styrene-ethylenepropylene-styrene-ethylenepropylene (SEPSEP), hydrogenated polybutadiene polymers such as styrene-ethylenebutylene-styrene (SEBS), styrene-ethylenebutylene-styrene-ethylenebutylene (SEBSEB), styrene-butadiene-styrene (SBS), styrene-isoprene-styrene (SIS), and hydrogenated poly-isoprene/butadiene polymer such as styrene-ethylene-ethylenepropylene-styrene (SEEPS). Polymer block configurations such as diblock, triblock, multiblock, star and radial are also contemplated in this invention.

In some instances, higher molecular weight block copolymers may be desirable. Block copolymers are available from Kraton Polymers U.S. LLC of Houston, Tex. under the designations KRATON G or D polymers, for example G1652, G1657, G1730, D1114, D1155, D1102, Septon Company of America, Pasadena, Tex. under the designations SEPTON 2004, SEPTON 4030, and SEPTON 4033, Dexco Polymers of Houston, Tex. under the designation VECTOR™ 4411. Another potential supplier of such polymers is Dynasol of Spain. Blends of such elastomeric resin materials are also contemplated as the primary component of the elastic film. Additionally, other desirable block copolymers are disclosed in U.S. Patent Publication 2003/0232928A1, which is incorporated by reference herein in its entirety.

Such base resins may be further combined with tackifiers and/or processing aids in compounds. Exemplary compounds include but are not limited to KRATON G2760, and KRATON G2755. Processing aids that may be added to the elastomeric polymer described above include a polyolefin to improve the processability of the composition. The polyolefin must be one which, when so blended and subjected to an appropriate combination of elevated pressure and elevated temperature conditions, is extrudable, in blended form, with the elastomeric base polymer. Useful blending polyolefin materials include, for example, polyethylene, polypropylene and polybutene, including ethylene copolymers, propylene copolymers and butene copolymers. A particularly useful polyethylene may be obtained from Eastman Chemical under the designation EPOLENE C-10. Two or more of the polyolefins may also be utilized. Extrudable blends of elastomeric polymers and polyolefins are disclosed in, for example, U.S. Pat. No. 4,663,220.

The type of material that is selected for the elastic layer 16 will be based on processing parameters and the physical properties of the material (among other factors). The elastic layer 16 may be attached to the auto-adhesive layer 12 and the cover layer 14 through any method that is known now or discovered in the future. Although the auto-adhesive layer 12, the cover layer 14 and the cover layer 16 are partially shown as layers of the same size, it should be noted that the layers may be different sizes and/or shapes. In addition, the elastic layer 16 may be the same (or different) thickness as the auto-adhesive layer 12 and the cover layer 14.

The type of auto-adhesive layer 12, cover layer 14 the cover layer 16 will be selected based on (i) processing parameters; (ii) physical properties; (iii) packaging issues; and (iv) costs (among other factors). The auto-adhesive layer 12, cover layer 14 and cover layer 16 should have properties that are required for a particular product and/or process. The physical properties of the auto-adhesive layer 12, the cover layer 14 and the cover layer 16 may be controlled to define properties such as melting temperature, shear strength, crystallinity, elasticity, hardness, tackiness and heat stability (among other properties).

It should be noted that any of the adhesive layer 12, cover layer 14 and elastic layer 16 may include additional materials that do not adversely affect the desired properties of the fastening system 10. Some example materials that may be added to the adhesive layer 12, cover layer 14 and/or elastic layer 16 include amorphous poly(alpha olefins), pigments, antioxidants, stabilizers, surfactants, waxes, flow promoters, solid solvents, plasticizers, nucleating agents and particulates (among others). If additional materials are included in one or more of the layers that make up the fastening system, it may be desirable that such additional materials be used in an amount that is less than about 5 weight percent (wherein the weight percent is based on the total weight amount of the fastening system).

The fastening system 10 of the present invention may be useful in a variety of applications. As an example, the fastening system 10 may be especially well suited to diaper-related applications because the auto-adhesive layer 12 is not readily contaminated. In addition, the auto-adhesive properties of the auto-adhesive layer 12 may reduce contamination of the fastening system 10 with many of the materials that are commonly present in diaper changing environments (e.g., baby lotions, oils and powders).

The fastening system 10 may be secured to diapers using thermal bonding and/or adhesives (among other techniques). As an example, the fastening system 10 may be secured to one portion of a diaper such that the fastening system is designed to engage a similar fastening system (e.g., a landing zone) on another portion of the diaper. The cover layer 14 may allow the auto-adhesive layer 12 to be safely and readily exposed when it is desired to adhere the fastening system 10 to an item.

The fastening system 10 may incorporated into a variety of products such as training pants, adult incontinent products, bed pads, catamenial devices (e.g., sanitary napkins), tampons, wipes, bibs, wound dressings, surgical capes or drapes, soiled garment bags, garbage bags, storage bags and product packaging.

As part of fabricating fastening system 10, multiple fastening systems may be cut from a sheet that is feed out from a continuous roll. The multiple fastening systems may then be stacked for packaging or alternatively delivered as the continuous roll. In some forms, the multiple fastening systems may be inter-folded, o-folded and/or compressed into various geometric shapes. In addition, the fastening systems 10 may be embossed with logos, use instructions or any other design or information.

The fastening system 10 may be in any form or shape that facilitates fastening one item to another. The fastening systems 10 may also be decorative in color and/or shape depending on consumer appeal. There are also embodiments that are contemplated where the fastening system 10 has a clear and/ or unobtrusive product form such that the fastening system 10 is discreet and does not interfere with the aesthetics of the products where the fastening system 10 is located.

A method of joining a fastening system to an item will now be described with reference to FIGS. 1-6. The method includes positioning a fastening system 10 near the item 30 that is to be joined to the fastening system 10. The fastening system 10 is similar to any of the fastening systems 10 described above (see, e.g., FIGS. 1 and 3). The method further includes exposing an auto-adhesive layer 12 by stretching a cover layer 14 (see, e.g., FIGS. 2 and 4), and then engaging the auto-adhesive layer 12 on the fastening system with an auto-adhesive layer 32 on the item 30 (see, e.g., FIGS. 5 and 6).

In some forms of the method, the cover layer 14 includes a thermoplastic polymer that has polymer chains which are oriented in a substantially uniform direction X such that exposing the auto-adhesive layer 12 includes exposing the auto-adhesive layer 12 by stretching the cover layer 14 in a direction Y that is perpendicular to the substantially uniform direction X of the polymer chains. In some embodiments, exposing the auto-adhesive layer 12 by stretching the cover layer 14 may include rupturing the cover layer 14 (see, e.g., FIGS. 2, and 4).

FIG. 2 shows an example embodiment where exposing the auto-adhesive layer by stretching the cover layer includes exposing the auto-adhesive layer by stretching the cover layer and the auto-adhesive layer. It should be noted that other embodiments are contemplated where only the cover layer 14 is stretched relative to the auto-adhesive layer 12.

FIG. 4 shows an example embodiment where the fastening system 10 includes an elastic layer 16 such that exposing the auto-adhesive layer 12 includes stretching the cover layer 14, the adhesive layer 12 and the elastic layer 16. It should be noted that other embodiments are contemplated where only one (or both) of the cover layer 14 and the elastic layer 16 are stretched relative to the auto-adhesive layer 12. In some embodiments, the elastic layer 16 may have a hysteresis of less than 50% and a set value of less than 15%.

Figure 7:
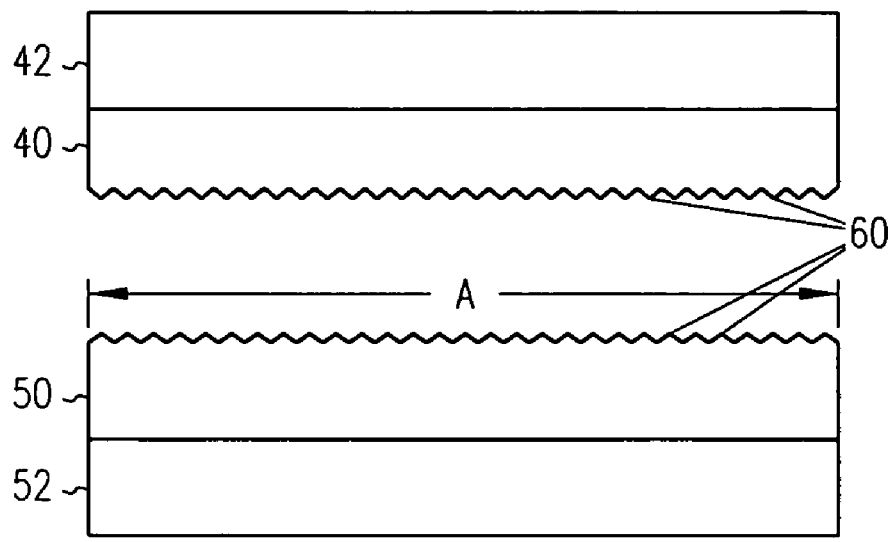
FIGS. 7-10 illustrate a fastening method.
Figure 8:
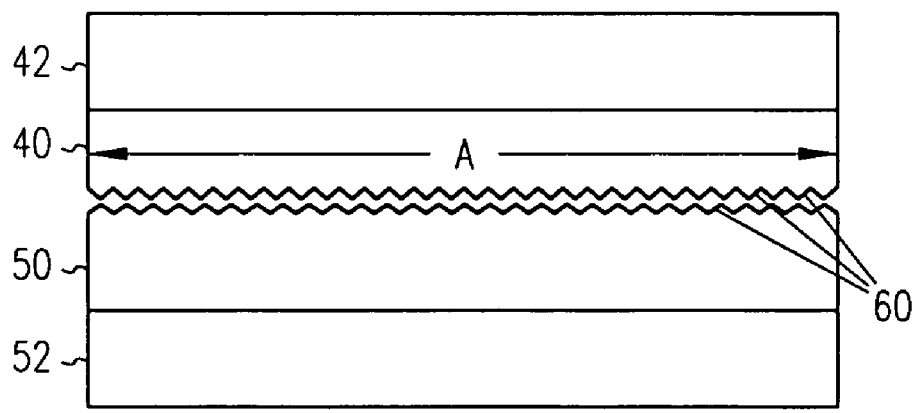
Figure 9:
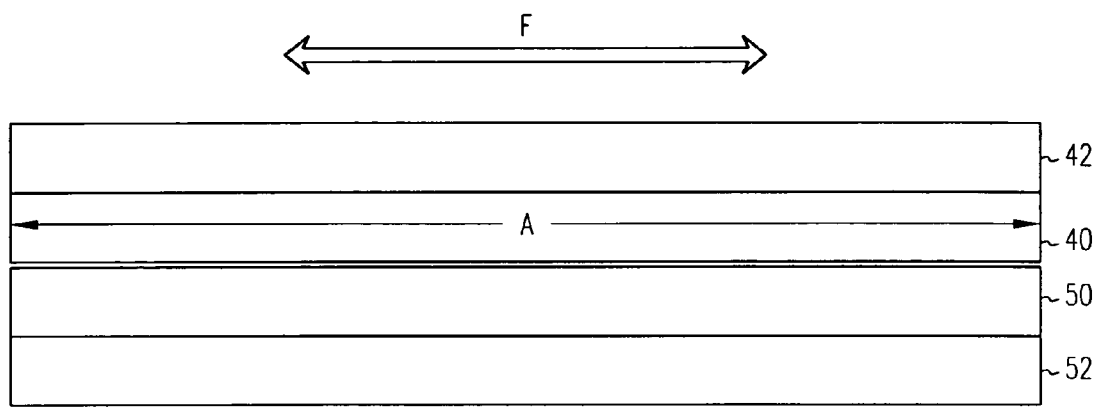
Figure 10:
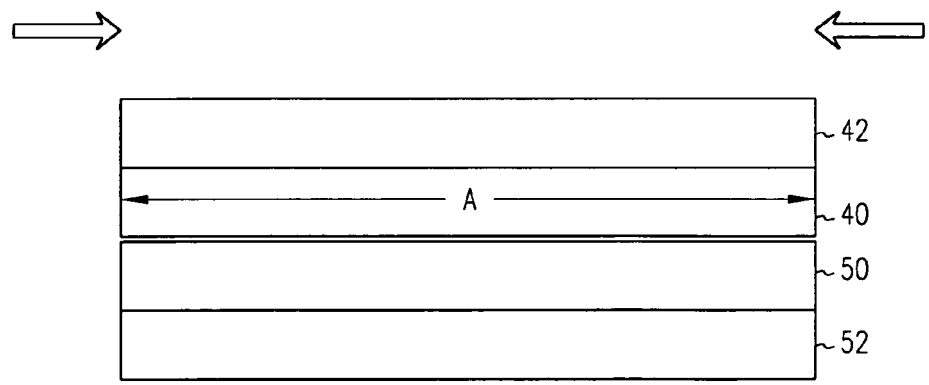

FIGS. 7-10 illustrate a fastening method that includes positioning a first auto-adhesive layer 40 near a second auto-adhesive layer 50 (see FIG. 7), and engaging the first auto-adhesive layer 40 with the second auto-adhesive layer 50 (see FIG. 8). As shown in FIG. 9, the method further includes applying a force F to the first and second auto-adhesive layers 40, 50 to stretch the first and second auto-adhesive layers 40, 50 and increase a bonding area A between the first and second auto-adhesive layers 40, 50. FIG. 10 shows that the method may further include removing the force F from the first and second adhesive layers.

As shown in FIGS. 7 and 8, each of the auto-adhesive layers 40, 50 may include imperfections 60 that negatively impact the degree of contact between the auto-adhesive layers 40, 50 in the bonding area A. It should be noted that the imperfections 60 which are shown in FIGS. 7 and 8 are exaggerated in size for purposes of illustration.

FIG. 9 shows that as the auto-adhesive layers 40, 50 are stretched, the bonding area A between the auto-adhesive layers 40, 50 increases, and the imperfections 60 on the auto-adhesive layers 40, 50 are somewhat smoothed out so that there is improved contact between the auto-adhesive layers 40, 50 in the bonding area A. The improved contact in the bonding area A results in improved joint strength between the auto-adhesive layers 40, 50.

It should be noted that applying a force F to the first and second adhesive layers 40, 50 to stretch the first and second adhesive layers 40, 50 may include at least doubling the bonding area A between the first and second adhesive layers 40, 50. In addition, applying a force F to the first and second auto-adhesive layers 40, 50 may include stretching the first and second auto-adhesive layers 40, 50 in multiple directions (only one direction is shown in FIGS. 7-10). The stretching of the first and second auto-adhesive layers 40, 50 may cause new areas of the first and second auto-adhesive layers 40, 50 to engage one another than would otherwise have been engaged without the stretching taking place.

In some embodiments, the first auto-adhesive layer 40 may be attached to a first elastic layer 42, and the second auto-adhesive layer 50 may be attached to a second elastic layer 52 such that applying a force to the first and second auto-adhesive layers 40, 50 further includes applying a force to the first and second elastic layers 42, 52. The first and second elastic layers 42, 52 may each have a hysteresis of less than 50% and a set value of less than 15%.

Depending on the applications where the auto-adhesive layers 40, 50 are used, it may be desirable for the auto-adhesive layers 40, 50 and/or the elastic layers 42, 52 to exhibit some particular elasticity. The Elastic Modulus of an item is meant to represent the amount of force that is initially required to stretch an item (which may be formed of one or more layers). Therefore, the Elastic Modulus represents the stiffness of the item.

When an item has an Elastic Modulus that is too low, the item may be too soft for adequate use. In addition, when the item has an Elastic Modulus that is too high, the item may require too much initial force in order to adequately stretch the item for an intended use.

While the invention has been described in detail with respect to specific embodiments, it will be appreciated that there are variations of, and equivalents to these embodiments. Accordingly, the scope of the present invention should be determined by the appended claims and any equivalents thereto.

What is claimed is:

1. A fastening system comprising:
a first auto-adhesive layer formed from a thermoplastic elastomer comprising a mixture of a polyethylene polymer and a block copolymer selected from the group consisting of poly(styrene)-co-poly (ethylene-butylene)-co-poly(styrene) copolymer and poly(styrene)-co-poly(ethylene-butylene) copolymer;
a cover layer that engages the first auto-adhesive layer, the first auto-adhesive layer being exposed through ruptures in the cover layer that occur when the cover layer is stretched; and
a second auto-adhesive layer which is formed from the same thermoplastic elastomer as the first auto-adhesive layer which engages the first auto-adhesive layer and is positioned on an item to which the first auto-adhesive layer affixes.

2. The fastening system of claim 1 wherein the cover layer is formed of a thermoplastic polymer that includes polymer chains.

3. The fastening system of claim 1 wherein the cover layer includes a blend of thermoplastics that have polymer chains.

4. The fastening system of claim 1 wherein the cover layer is formed of a non-woven material.

5. The fastening system of claim 4 wherein the non-woven material is a melt-blown fibrous material.

6. The fastening system of claim 1 wherein the cover layer has a density greater than 1.0 grams per cubic centimeter.

7. The fastening system of claim 1 wherein the first auto-adhesive layer exhibits a Peak Load of Auto-adhesive Strength value that is greater than about 400 grams per inch width of the auto-adhesive layer.

8. The fastening system of claim 1 further comprising an elastic layer that has a hysteresis of less than 50% and a set value of less than 15%, wherein the elastic layer is a styrenic block copolymer.

9. The fastening system of claim 8 wherein the elastic layer is in contact with the auto-adhesive layer.

10. The fastening system of claim 8 wherein the auto-adhesive layer is between the cover layer and the elastic layer.

* * * * *